(12) United States Patent
Mager et al.

(10) Patent No.: US 9,168,324 B2
(45) Date of Patent: Oct. 27, 2015

(54) PRODUCTION OF POLYURETHANE FOAMS FOR WOUND MANAGEMENT

(75) Inventors: Michael Mager, Leverkusen (DE); Michael Ludewig, Leverkusen (DE); Mathias Matner, Neuss (DE); Melita Dietze, Erkrath (DE); Burkhard Fugmann, Ratingen (DE)

(73) Assignee: Bayer MaterialScience AG (DE)

( * ) Notice: Subject to any disclaimer, the term of this patent is extended or adjusted under 35 U.S.C. 154(b) by 913 days.

(21) Appl. No.: 12/169,842

(22) Filed: Jul. 9, 2008

(65) Prior Publication Data

US 2009/0018480 A1 Jan. 15, 2009

(30) Foreign Application Priority Data

Jul. 10, 2007 (EP) .................................. 07013425

(51) Int. Cl.
*A61L 15/42* (2006.01)
*C08G 18/48* (2006.01)
*C08G 18/71* (2006.01)
*C08G 101/00* (2006.01)

(52) U.S. Cl.
CPC ........... *A61L 15/425* (2013.01); *C08G 18/4833* (2013.01); *C08G 18/718* (2013.01); *C08G 2101/00* (2013.01)

(58) Field of Classification Search
None
See application file for complete search history.

(56) References Cited

U.S. PATENT DOCUMENTS

| | | | | |
|---|---|---|---|---|
| 3,632,557 A * | 1/1972 | Brode et al. | ................... | 528/28 |
| 3,975,567 A | 8/1976 | Lock | | |
| 3,978,266 A | 8/1976 | Lock | | |
| 3,979,344 A * | 9/1976 | Bryant et al. | ................... | 528/22 |
| 4,222,925 A * | 9/1980 | Bryant et al. | ................. | 524/589 |
| 4,502,479 A * | 3/1985 | Garwood et al. | ................. | 602/8 |
| 4,619,578 A * | 10/1986 | Routledge | ..................... | 414/498 |
| 4,667,661 A * | 5/1987 | Scholz et al. | ..................... | 602/8 |
| 4,774,937 A * | 10/1988 | Scholz et al. | ..................... | 602/8 |
| 5,409,472 A * | 4/1995 | Rawlings et al. | ............. | 604/307 |
| 5,423,735 A * | 6/1995 | Callinan et al. | .................... | 602/8 |
| 5,540,652 A * | 7/1996 | Callinan et al. | .................... | 602/1 |
| 5,603,691 A * | 2/1997 | Scholz et al. | ..................... | 602/8 |
| 5,714,257 A * | 2/1998 | Shah et al. | .................... | 428/391 |
| 5,744,528 A * | 4/1998 | Callinan et al. | ............... | 524/265 |
| 5,925,004 A * | 7/1999 | Doubleday et al. | ............... | 602/6 |
| 5,984,884 A * | 11/1999 | Alvarez et al. | .................... | 602/6 |
| 6,077,240 A * | 6/2000 | Sholz et al. | ....................... | 602/8 |
| 6,369,188 B1 * | 4/2002 | Rappoport et al. | ............. | 528/49 |
| 6,596,786 B2 * | 7/2003 | Purvis et al. | .................... | 522/35 |
| 6,762,270 B2 * | 7/2004 | Ludewig et al. | ................ | 528/28 |
| 6,979,713 B2 * | 12/2005 | Barber, Jr. | ..................... | 525/124 |
| 7,183,331 B2 * | 2/2007 | Kiso et al. | ..................... | 521/129 |

FOREIGN PATENT DOCUMENTS

| | | |
|---|---|---|
| CN | 1184496 A | 6/1998 |
| DE | 19831285 A1 | 1/2000 |
| DE | 19831285 A1 * | 1/2000 |
| EP | 0059048 A1 | 9/1982 |
| WO | WO-94/23768 A1 | 10/1994 |
| WO | WO 9423768 A1 * | 10/1994 |
| WO | WO-9629374 A1 | 9/1996 |
| WO | WO-00/04069 A1 | 1/2000 |
| WO | WO-2007025668 A1 | 3/2007 |

OTHER PUBLICATIONS

Desmodur VKS 70, Scifinder, CAS #83441-86-5, Oct. 13, 2014.*
Office Action in CN 200880023844.0.

* cited by examiner

*Primary Examiner* — James J Seidleck
*Assistant Examiner* — Peter A Salamon
(74) *Attorney, Agent, or Firm* — Drinker Biddle & Reath LLP

(57) ABSTRACT

The present invention provides novel polyurethane-based wound dressing foams, obtained by foaming and curing silane-terminated polyurethanes.

20 Claims, No Drawings

PRODUCTION OF POLYURETHANE FOAMS FOR WOUND MANAGEMENT

CROSS-REFERENCE TO RELATED APPLICATIONS

This application claims benefit to European Pat. App. No. 07013425.9, filed Jul. 10, 2007, the disclosure of which is incorporated by reference in its entirety.

BACKGROUND OF THE INVENTION

The use of wound dressing foams for managing weeping wounds is prior art. Owing to their high absorbency and their good mechanical properties, polyurethane foams produced by reaction of mixtures of diisocyanates and polyols or NCO-functional polyurethane prepolymers with water in the presence of certain catalysts and also (foam) additives are generally used. Aromatic diisocyanates are generally employed, since they are best foamable. Numerous forms of these processes are known, for example described in U.S. Pat. No. 3,978,266, U.S. Pat. No. 3,975,567 and EP-A 0 059 048. However, the aforementioned processes have the disadvantage that they require the use of reactive mixtures, comprising diisocyanates or appropriate NCO-functional prepolymers, whose handling is technically inconvenient and costly, since appropriate protective measures are necessary for example. Direct application of these mixtures to (human) skin is not possible because of the high reactivity of the isocyanate groups present.

As well as through the use of compositions comprising free isocyanate groups, polyurethane foams can also be produced using silane-terminated polyurethane prepolymers which are foamable through use of blowing agents. Numerous embodiments are known for producing sealing and insulating foams, for example described in EP-A 1 098 920. The use of the compositions for producing wound dressing foams was hitherto not recognized. Nor have the critical requirements for use as wound dressing foams, such as good water vapour permeability and high liquid uptake capacity, hitherto been described.

BRIEF SUMMARY OF THE INVENTION

The present invention provides novel polyurethane-based wound dressing foams, obtained by foaming and curing silane-terminated polyurethanes.

It is an object of the present invention to provide polyurethane wound dressing foams which avoid the abovementioned disadvantages of using isocyanato-containing, reactive mixtures.

It has now been found that silane-terminated polyurethane prepolymers (STPs), surprisingly, are likewise very useful as wound dressing foams for medical applications after foaming and curing through crosslinking of the silane groups.

The present invention accordingly provides for the use of foams obtainable from silane-terminated polyurethane prepolymers as wound dressing foams.

The present invention further provides a process for producing wound dressing foams wherein a composition comprising
a) silane-terminated polyurethane prepolymers (I)
b) (foam) additives (II)
c) optionally catalysts (III),
d) optionally blowing agents (IV), and also
e) optionally further, auxiliary and adjunct materials (V)
is foamed, applied to a substrate before, during or after foaming and finally cured in the presence of water.

The present invention further provides the wound dressing foams obtainable by the process of the invention.

The invention further provides for the use of compositions comprising
a) silane-terminated polyurethane prepolymers (I) comprising more than one alkoxysilane group
b) (foam) additives (II)
c) optionally catalysts (III),
d) optionally blowing agents (IV), and also
e) optionally further, auxiliary and adjunct materials (V)
for producing dressing foams for wound management.

DETAILED DESCRIPTION OF THE INVENTION

As used herein, the singular terms "a" and "the" are synonymous and used interchangeably with "one or more" and "at least one," unless the language and/or context cleary indicates otherwise. Accordingly, for example, reference to "a substrate" herein or in the appended claims can refer to a single substrate or more than one substrate. Additionally, all numerical values, unless otherwise specifically noted, are understood to be modified by the word "about."

Polyurethane foam wound dressing foams herein are porous materials, preferably having at least partly an open-cell content, which consist essentially of polyurethanes crosslinked via siloxane bonds Si—O—Si and protect wounds by closing out germs or ambient effects, provide rapid and high absorption of physiological saline or exudate and ensure optimal wound conditions through suitable perviousness to moisture.

Silane-terminated polyurethane prepolymers (I) for the purposes of the invention include all (pre)polymers having more than one urethane group and more than one alkoxysilane group, which are capable in the presence of water and if appropriate catalysts (III) of reacting via siloxane bonds Si—O—Si to form crosslinked polyurethanes.

Such silane-terminated prepolymers are obtainable by reacting
polyurethane prepolymers (A) having free isocyanate groups to an average NCO functionality of at least 1.5 with
di- and/or trialkoxysilanes (B) having amino, hydroxyl and/or thiol groups bonded to the silicon atom via an alkylene radical,
or
polyhydroxy compounds (C) having an average OH functionality of at least 1.5 with
di- and/or trialkoxysilanes (D) having isocyanate and/or isothiocyanate groups bonded to the silicon atom via an alkylene radical.

The polyurethane prepolymers (A), which contain free isocyanate groups, are obtainable in a conventional manner by the reaction of organic polyisocyanates with polyhydroxy compounds having a functionality of 1.5 to 6 by using the organic polyisocyanates in excess (molar ratio NCO/OH>1).

Suitable polyisocyanates include the well-known aromatic, araliphatic, aliphatic or cycloaliphatic polyisocyanates having an average NCO functionality of ≥2.

Examples of such suitable polyisocyanates are 1,4-butylene diisocyanate, 1,6-hexamethylene diisocyanate (HDI), isophorone diisocyanate (IPDI), 2,2,4 and/or 2,4,4-trimethylhexamethylene diisocyanate, the isomeric bis(4,4'-isocyanatocyclohexyl)methanes or their mixtures of any desired isomer content, 1,4-cyclohexylene diisocyanate, 1,4-phenylene diisocyanate, 2,4- and/or 2,6-toluylene diisocyanate, 1,5-naphthylene diisocyanate, 2,2'- and/or 2,4'- and/or 4,4'- diphenylmethane diisocyanate, 1,3- and/or 1,4-bis(2-isocyanatoprop-2-yl)benzene (TMXDI), 1,3-bis(isocyanatomethyl)benzene (XDI), and also alkyl 2,6-diisocyanatohexanoate (lysine diisocyanates) having $C_1$-$C_8$-alkyl groups, and 4-isocyanatomethyl-1,8-octane diisocyanate (nonane triisocyanate) and triphenylmethane 4,4',4''-triisocyanate.

As well as the aforementioned polyisocyanates, it is also possible to use, proportionally, modified diisocyanates or triisocyanates of uretdione, isocyanurate, urethane, allophanate, biuret, iminooxadiazinedione and/or oxadiazinetrione structure.

Preferably, the polyisocyanates or polyisocyanate mixtures of the aforementioned kind have exclusively aliphatically and/or cycloaliphatically attached isocyanate groups and an average NCO functionality in the range from 2 to 4, preferably in the range from 2 to 2.6 and more preferably in the range from 2 to 2.4. It is particularly preferable to utilize 1,6-hexamethylene diisocyanate, isophorone diisocyanate, the isomeric bis(4,4'-isocyanatocyclohexyl)methanes, and also mixtures thereof.

Useful polyhydroxy compounds for component (C) include all well-known polyurethane coating technology polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols that have an average OH functionality of at least 1.5. These can be used individual or in any desired mixtures with each or one another. Preference, however, is given to using polyether polyols.

Polyester polyols for component (C) are the well-known polycondensates formed from di- and also optionally tri- and tetraols and di- and also optionally tri- and tetracarboxylic acids or hydroxy carboxylic acids or lactones. Instead of the free polycarboxylic acids it is also possible to use the corresponding polycarboxylic anhydrides or corresponding polycarboxylic esters of lower alcohols for preparing the polyesters.

Examples of suitable diols for producing polyester polyols are ethylene glycol, butylene glycol, diethylene glycol, triethylene glycol, polyalkylene glycols such as polyethylene glycol, also 1,2-propanediol, 1,3-propanediol, butanediol(1,3), butanediol(1,4), hexanediol(1,6) and isomers, neopentyl glycol or neopentyl glycol hydroxypivalate, of which hexanediol(1,6) and isomers, neopentyl glycol and neopentyl glycol hydroxypivalate are preferred. Trimethylolpropane, glycerol, erythritol, pentaerythritol, trimethylolbenzene or trishydroxyethyl isocyanurate are suitable, for example, as triols and tetraols.

Useful dicarboxylic acids include phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethyl glutaric acid and/or 2,2-dimethylsuccinic acid. The corresponding anhydrides can also be used as a source of acid. Preferred acids are aliphatic or aromatic acids of the aforementioned kind. Adipic acid, isophthalic acid and optionally trimellitic acid are particularly preferred.

Hydroxy carboxylic acids useful as reaction participants in the preparation of a polyester polyol having terminal hydroxyl groups include for example hydroxycaproic acid, hydroxybutyric acid, hydroxydecanoic acid, hydroxystearic acid and the like. Suitable lactones include caprolactone, butyrolactone and homologues. Caprolactone is preferred.

Useful polyhydroxy compounds for component (C) further include polycarbonates, preferably polycarbonate diols, having number average molecular weights $M_n$ in the range from 400 to 8000 g/mol, preferably in the range from 600 to 3000 g/mol. These are obtainable in a conventional manner by reaction of carbonic acid derivatives, such as diphenyl carbonate, dimethyl carbonate or phosgene, with polyols, preferably diols.

Examples of diols useful for preparing polycarbonates are ethylene glycol, 1,2-propanediol, 1,3-propanediol, 1,3-butanediol, 1,4-butanediol, 1,6-hexanediol, 1,8-octanediol, neopentyl glycol, 1,4-bishydroxymethylcyclohexane, 2-methyl-1,3-propanediol, 2,2,4-trimethyl-1,3-pentanediol, dipropylene glycol, polypropylene glycols, dibutylene glycol, polybutylene glycols, bisphenol A and lactone-modified diols of the aforementioned kind.

The polycarbonate diol preferably contains 40% to 100% by weight of hexanediol, preference being given to 1,6-hexanediol and/or hexanediol derivatives based on the underlying diols. Such hexanediol derivatives are based on hexanediol and have ester or ether groups as well as terminal OH groups. Such derivatives are obtainable by reaction of hexanediol with excess caprolactone or by etherification of hexanediol with itself to form di- or trihexylene glycol.

Useful polyhydroxy compounds for component (C) further include polyether polyols. Suitable are for example the polytetramethylene glycol polyethers which are known per se in polyurethane chemistry and are obtainable by polymerization of tetrahydrofuran by means of cationic ring opening.

Preferred polyether polyols for component (C) include the well-known addition products of styrene oxide, ethylene oxide, propylene oxide, butylene oxides and/or epichlorohydrin onto di- or polyfunctional starter molecules, of which addition products of ethylene oxide or propylene oxide, and also mixtures of those mentioned, are particularly preferred. Very particular preference is given to addition products of ethylene oxide and propylene oxide in each of which the weight fraction of ethylene oxide is at least 5% to 80% by weight, preferably 10% to 65% by weight and more preferably 10% to 30% by weight, this weight fraction being based on the total of ethylene oxide and propylene oxide units present in the addition product, plus the starter molecules used.

The alkoxylation with ethylene oxide or propylene oxide can take place under base catalysis or through use of double metal cyanide (DMC) compounds.

Useful starter molecules for preparing the polyether polyols of component (C) include all prior art low molecular weight polyols, organic polyamines and/or water, for example butyl diglycol, glycerol, diethylene glycol, trimethylolpropane, propylene glycol, sorbitol, ethylenediamine, triethanolamine, 1,4-butanediol. Preferred starter molecules are water, ethylene glycol, propylene glycol, 1,4-butanediol, diethylene glycol, butyl diglycol or any mixtures thereof.

The number average molecular weight $M_n$ of the polyether polyols is preferably in the range from 300 to 20 000 g/mol, more preferably in the range from 1000 to 12 000 g/mol and most preferably in the range from 2000 to 6000 g/mol.

Reaction of organic di- or polyisocyanates with polyhydroxy compounds having a functionality of 1.5 to 6 in an NCO/OH molar ratio <1 gives polyhydroxy compounds having urethane groups and likewise useful as component (C).

Di- and/or trialkoxysilanes having amino, hydroxyl and/or thiol groups and useful for component (B) are well known to a person skilled in the art, examples being aminopropyltrimethoxysilane, mercaptopropyltrimethoxysilane, aminopropylmethyldimethoxysilane, mercaptopropylmethyldimethoxysilane, aminopropyltriethoxysilane, mercaptopropyltriethoxysilane, aminopropylmethyldiethoxysilane, mercaptopropylmethyldiethoxysilane, aminomethyltrimethoxysilane, aminomethyltriethoxysilane, (aminomethyl)methyldimethoxysilane, (aminome-thyl)methyldiethoxysilane, N-butylaminopropyltrimethoxysilane, N-ethylaminopropyltrime-thoxysilane, N-phenylaminopropyltrimethoxysilane, diethyl N-(3-triethoxysilylpropyl)aspartate, diethyl N-(3-trimethoxysilylpropyl)aspartate and diethyl N-(3-dimethoxymethysilylpropyl)aspartate. The use of diethyl N-(3-trimethoxysilylpropyl)aspartate and aminopro-pyltrimethoxysilane is preferred.

Di- and/or trialkoxysilanes having isocyanate and/or isothiocyanate groups and useful for component (D) are likewise known in principle.

Examples are isocyanatomethyltrimethoxysilane, isocyanatomethyltriethoxysilane, (isocyana-tomethyl)methyldimethoxysilane, (isocyanatomethyl)methyldiethoxysilane, 3-isocyanatopropyl-trimethoxysilane, 3-isocyanatopropylmethyldimethoxysilane, 3-isocyanatopropyltriethoxysilane and 3-isocyanatopropylmethyldiethoxysilane. Preference is here given to the use of 3-isocyanatopropyl-trimethoxysilane and 3-isocyanatopropyltriethoxysilane.

The additives (II) are nonionic, anionic, cationic or zwitterionic surfactants or mixtures thereof, which serve in the compositions of the invention to improve foam formation, foam stability or the properties of the resulting polyurethane foam. Preferred additives (II) are nonionic surfactants, more preferably nonionic surfactants based on polyether siloxanes.

The preferred additives (II) have not only a stabilizing effect but also a particularly advantageous influence with regard to the hydrophilicization of the foams, which manifests itself in moisture uptake quantity and rate.

Useful catalysts (III) for inclusion in the compositions of the invention include in principle all materials known per se from silicon chemistry which catalyse the hydrolysis and condensation of alkoxysilanes and silanol groups, respectively. Examples are metal salts, metal complexes, organometallic compounds and also acids and bases. Preference is given to use of organic and inorganic acids or bases and particular preference to the use of organic or inorganic acids such as for example hydrochloric acid or p-toluenesulphonic acid. When catalysts (III) are used in the compositions, they are preferably dissolved in water which is also required for the actual crosslinking of the foams.

Blowing agents (IV) can most simply be air or nitrogen, but it is of course also possible to use any other blowing agents for foaming the composition of the invention which are known per se from polyurethane chemistry. Examples are n-butane, i-butane, propane and dimethyl ether and also mixtures thereof.

Useful auxiliary and adjunct materials (V) include for example fillers, thickeners or thixotroping agents, antioxidants, light stabilizers, plasticizers, pigments and/or flow control agents.

Preferred auxiliary and adjunct materials are fillers, preferably inorganic fillers, which can contribute to improving the mechanical properties of the polyurethane foam of the invention. Useful examples include chalks and finely divided silicas, in particular fumed silicas.

Useful plasticizers include any natural or synthetic material sufficiently compatible with the polyurethane foam. Examples of suitable plasticizers are camphor, esters of (aliphatic) dicarboxylic acids, for example of adipic acid, polyesters, in particular based on adipic, sebacic, azelaic and phthalic acid acid condensed with 1,3-butanediol, 1,4-butanediol or 1,6-hexanediol, and also phosphoric esters, fatty acid esters and hydroxy carboxylic esters (for example based on citric acid, tartaric acid or lactic acid).

Curing by crosslinking the alkoxysilane groups to form siloxane bridges takes place in the presence of water, which can be directly added in liquid form, for example as a solvent for the catalyst, or can come from the air in the form of atmospheric humidity.

The compositions essential to the invention typically contain, based on dry substance, 80 to 99.9 parts by weight of the silane-terminated polyurethane prepolymer (I) and 0.1 to 20 parts by weight of the (foam) additive (II). Preferably, the compositions contain, based on dry substance, 85 to 99.9 parts by weight of silane-terminated polyurethane prepolymer (I) and 0.1 to 15 parts by weight of (foam) additive (II), more preferably 95 to 99.9 parts by weight of (I) and 0.1 to 5 parts by weight of (II).

Auxiliary and adjunct materials (V) are typically added in amounts of 0 to 50 parts by weight, preferably 10 to 40 parts by weight.

Water added for crosslinking beyond ambient moisture is typically added in an amount such that the molar ratio of alkoxy groups to added water is less than or equal to 1 (excess water). The molar ratio is preferably less than or equal to 0.75 and more preferably less than or equal to 0.55.

The blowing agent or blowing agent mixture (IV) is typically used in an amount of 1% to 50% by weight, preferably 5% to 40% by weight and more preferably 5% to 20% by weight, the sum total of the employed components (I), (II) and optionally (III), (IV), (V) being 100% by weight.

The mixing of components (I) and (II) can take place in any order, as can the mixture with the optional components (III) to (V).

Preferably, components (I) and (II) and also optionally (III) to (V) are each provided separately; that is, the reactive component (I) is provided in the absence of water and the optional catalyst (III). This gives a composition which is stable in storage at 23° C. for at least 6 months (stable in storage is to be understood as meaning an increase in the viscosity of the mixture of less than 50%, preferably less than 25% and more preferably less than 15% based on the starting level of the composition).

Foaming in the process of the invention is accomplished by shaking of the composition, mechanical stirring at high speeds of rotation or by decompressing a blowing gas. After or during foaming, the composition undergoes curing to obtain the desired polyurethane foam. Before complete solidification or curing, i.e. as long as the composition is still flowable, it can be applied to a suitable substrate by common application techniques such as pouring or blade coating. In addition, the composition can be applied directly to human or animal skin, in which case foaming and curing then generally take place simultaneously.

Mechanical foaming can be effected using any desired mechanical stirring, mixing and dispersing techniques. Air is generally introduced in the process, but nitrogen and other gases can also be used for this purpose.

The foam thus obtained is, in the course of foaming or immediately thereafter, applied to a substrate or introduced into a mould and cured.

Application to a substrate can be for example by pouring or blade coating, but other conventional techniques are also possible. Multilayer application with optionally intervening curing steps is also possible in principle.

A satisfactory curing rate for the foams is observed at a temperature as low as 20° C. However, higher temperatures of preferably more than 30° C. can also be employed for faster curing and fixing of the foams, for example with the aid of conventional heating and drying apparatus, such as (circulating air) drying cabinets, hot air or IR radiators.

The compositions may be applied, after foaming or while foaming, directly to the skin or, in the course of an industrial manufacture of wound dressing foams, to release papers or foils/films which facilitate simple detachment of the wound contact material before its use for covering an injured site.

Application and curing can each be carried out batchwise or continuously, but an entirely continuous process is preferable for the industrial manufacture of wound dressing foams.

When the composition is applied directly, by spraying for example, to human or animal skin, curing likewise takes place very rapidly at ambient conditions and as a result of the body's temperature, respectively. The assistance of an external source of heat is similarly possible here, although not preferable.

In one embodiment of the present invention, the silane-terminated polyurethane prepolymer (I) is mixed with the additive (II) and optionally further, auxiliary and adjunct materials (V). After foaming of the mixture, for example due to mechanical incorporation of air or of some other gas, catalyst (III) is added, the (foamed) mixture is applied to a suitable substrate and finally cured in the presence of atmospheric humidity. To speed the curing of the foamed mixture, moreover, water can be added, which is preferably done together with the (dissolved) catalyst (III).

In a further embodiment of the present invention, the silane-terminated polyurethane prepolymer (I) is mixed with the additive (II) and optionally further, auxiliary and adjunct materials (V) and transferred into a suitable pressure container, for example a spray can. Thereafter, the blowing agent (IV) is added; as the mixture is applied to a suitable substrate, it foams and is cured through atmospheric humidity.

In a further embodiment of the present invention, the silane-terminated polyurethane prepolymer (I) is mixed with the additive (II) and optionally further, auxiliary and adjunct materials (V) and transferred into a first chamber of a suitable pressure container, for example into a spray can, the pressure container having at least 2 separate chambers. Catalyst (III), which is preferably mixed with a suitable amount of water, is introduced into a second chamber of the pressure container. The auxiliary and adjunct materials (V) can also be admixed in the second chamber, but this is less preferably. Then, the blowing agent (IV) is added to either or both of the chambers and, finally, the two-component mixture is applied to a suitable substrate, and at the same time foaming and curing takes place.

Before curing, the foam densities of the polyurethane foams are typically in the range from 50 to 800 g/liter, preferably in the range from 100 to 500 g/liter and more preferably in the range from 100 to 250 g/liter (mass of all input materials [in g] based on the foam volume of one liter).

After drying, the polyurethane foams have a microporous, at least partially open-cell structure comprising intercommunicating cells. The density of the cured foams is typically below 0.4 g/cm$^3$, preferably less than 0.35 g/cm$^3$ and more preferably in the range from 0.01 to 0.2 g/cm$^3$.

The DIN EN 13726-1 Part 3.2 physiological saline absorbency is typically 100 and 1500% and preferably in the range from 300 to 800% for the polyurethane foams (mass of liquid taken up, based on mass of dry foam). The DIN EN 13726-2 Part 3.2 vapour transmission rate is typically in the range from 500 to 8000 g/24 h*m$^2$, preferably in the range from 1000 to 6000 g/24 h*m$^2$ and more preferably in the range from 2000 to 5000 g/24 h*m$^2$.

The polyurethane foams exhibit good mechanical strength and high elasticity. Typically, maximum stress is greater than 0.1 N/mm$^2$ and maximum extension is greater than 100%. Preferably, extension is greater than 200% (determined according to DIN 53504).

After curing, the thickness of the polyurethane foams is typically in the range from 0.1 mm to 50 mm, preferably in the range from 0.5 mm to 20 mm, more preferably in the range from 1 to 10 mm and most preferably in the range from 1 to 5 mm.

The polyurethane foams can moreover be adhered, laminated or coated to or with further materials, for example materials based on hydrogels, (semi-) permeable films, coatings, hydrocolloids or other foams.

It is likewise possible to add, incorporate or coat with antimicrobially or biologically active components which for example have a positive effect with regard to wound healing and the avoidance of germ loads.

The invention will now be described in further detail with reference to the following non-limiting examples.

EXAMPLES

Unless indicated otherwise, all percentages are by weight.

NCO contents were unless expressly mentioned otherwise determined volumetrically in accordance with DIN-EN ISO 11909.

Substances and abbreviations used:
PO propylene oxide
EO ethylene oxide
DBTL dibutyltin dilaurate
Tegostab® B 1048 polyethersiloxane (from Degussa, Düsseldorf; Germany)
Aerosil® R 9200 finely divided, fumed silica (from Degussa, Düsseldorf, Germany)
Mesamoll® plasticizer based on an alkylsulphonic ester (from Lanxess, Leverkusen, Germany)

Preparation of silane-terminated prepolymer 1 (STP 1):

A mixture of 2003.6 g of a difunctional, ethoxylated polyether (OH number 28, molecular weight 4000 g/mol, PO/EO ratio=6.5), 214.3 g of 3-isocyanatotrimethoxysilane and 133 μl of DBTL was heated to 60° C. with stirring until the NCO content was 0.

Example 1

Production of a Foam by Base Catalysis 117.5 g of STP 1 and 3.8 g of Tegostab® B 1048 were mixed in a plastic beaker using a hand stirrer and foamed to a volume of about 300 ml over 10 min. Thereafter, 2.5 g of aqueous potassium hydroxide solution (1.25 mol/L) were added, whereupon curing took place within 20 s. A white foam was obtained.

Example 2

Production of Foams by Acid Catalysis 117.5 g of STP 1 and 3.8 g of Tegostab® B 1048 were mixed in a plastic beaker using a hand stirrer and foamed to a volume of about 300 ml over 10 min. Thereafter, 2.5 g of a 5% aqueous solution of p-toluenesulphonic acid were added, whereupon curing took place within 20 s. A white foam was obtained.

Experiment a) was repeated with 2 g of a 20% aqueous solution of p-toluenesulphonic acid. Curing to form a white foam took place after just 50 s.

Example 3

Foam with Filler and Plasticizer

A dissolver was used to initially disperse 50 g of Aerosil® R 9200 in 117.5 g of STP 1 (almost transparent dispersion). Thereafter, 25 g of Mesamoll® and 3.8 g of Tegostab® B 1048 were added, and finally the mixture was foamed in a plastic beaker with a hand stirrer to a volume of about 300 ml over 10 min. After addition of 2.5 g of a 5% aqueous solution of p-toluenesulphonic acid, curing to form a white foam was achieved within 20 s.

All documents mentioned herein are incorporated by reference to the extent relevant to making, using or describing the present invention.

What is claimed is:

1. A process for producing a wound dressing foam, comprising providing a composition comprising:
   (a) silane-terminated polyurethane prepolymers (I) obtained by reacting:
      (i) polyurethane prepolymers (A) having free isocyanate groups to an average NCO functionality of at least 1.5 with;
      (ii) di- and/or trialkoxysilanes (B) having amino, hydroxyl and/or thiol groups bonded to the silicon atom via an alkylene radical; or
      (iii) polyhydroxy compounds (C) having an average OH functionality of at least 1.5 with;
      (iv) di- and/or trialkoxysilanes (D) having isocyanate and/or isothiocyanate groups bonded to the silicon atom via an alkylene radical comprising more than one alkoxysilane group;
   (b) (foam) additives (II);
   (c) optionally catalysts (III);
   (d) optionally blowing agents (IV), and also
   (e) optionally further, auxiliary and adjunct materials (V);
   wherein the composition is foamed, applied to skin before, during or after foaming, and cured in the presence of water, and
   wherein said wound dressing foam has a density of less than 0.4 g/cm$^3$ and
   wherein water is added for curing, in an amount such that the molar ratio of alkoxysilane groups in the silane-terminated prepolymer to added water is less than or equal to 1.

2. A wound dressing foam on an animal or human skin obtained by the process as claimed in claim 1 and comprising a silane-terminated polyurethane prepolymer, wherein said wound dressing foam has a density of less than 0.4 g/cm$^3$, and wherein said wound dressing foam is present on the animal or human skin.

3. The process according to claim 1, wherein the silane-terminated prepolymers (I) are based on polyisocyanates or polyisocyanate mixtures having exclusively aliphatically and/or cycloaliphatically bound isocyanate groups and an average NCO functionality of 2 to 4.

4. The process according to claim 1, wherein the additives (II) comprise nonionic surfactants based on polyether siloxanes.

5. The process according to claim 1, wherein the compositions to be foamed comprise, based on dry substance, 85 to 99.9 parts by weight of silane-terminated polyurethane prepolymer (I) and 0.1 to 15 parts by weight of the (foam) additive (II) and also 0 to 50 parts by weight of auxiliary and adjunct materials (V).

6. A wound dressing foam obtained by the process of claim 1.

7. A wound dressing foam obtained by the process of claim 1 and comprising a silane-terminated polyurethane prepolymer, wherein said wound dressing foam is adhered to or laminated with or coated with a permeable or semi-permeable film.

8. A wound dressing foam obtained by the process of claim 1 and comprising a silane-terminated polyurethane prepolymer, wherein said wound dressing foam comprises an antimicrobially or biologically active component.

9. The wound dressing foam of claim 2, wherein said wound dressing foam has a density of less than 0.35 g/cm$^3$.

10. The wound dressing foam of claim 2, wherein said wound dressing foam has a density in the range of from 0.01 to 0.2 g/cm$^3$.

11. The process of claim 1, wherein said wound dressing foam has a density of less than 0.35 g/cm$^3$.

12. The process of claim 1, wherein said wound dressing foam has a density in the range of from 0.01 to 0.2 g/cm$^3$.

13. The process according to claim 4, wherein the compositions to be foamed comprise, based on dry substance, 85 to 99.9 parts by weight of silane-terminated polyurethane prepolymer (I) and 0.1 to 15 parts by weight of the (foam) additive (II) and also 0 to 50 parts by weight of auxiliary and adjunct materials (V).

14. The process according to claim 13, wherein the silane-terminated prepolymers (I) are based on polyisocyanates or polyisocyanate mixtures having exclusively aliphatically and/or cycloaliphatically bound isocyanate groups and an average NCO functionality of 2 to 2.4.

15. The process according to claim 1, wherein component C includes the addition of styrene oxide, ethylene oxide, propylene oxide, butylene oxide or epichlorohydrin or a mixture thereof.

16. The process according to claim 1, wherein component C includes the addition of ethylene oxide and propylene oxide in an amount from 10 to 65% by weight.

17. The process according to claim 1, wherein component C includes the addition of ethylene oxide and propylene oxide in an amount from 10 to 30% by weight.

18. The process according to claim 14, wherein component C includes the addition of ethylene oxide and propylene oxide in an amount from 10 to 30% by weight.

19. The process according to claim 1, wherein the molar ratio of alkoxysilane groups in the silane-terminated prepolymer to added water is less than 1.

20. The process according to claim 18, wherein the molar ratio of alkoxysilane groups in the silane-terminated prepolymer to added water is less than 1.

* * * * *